United States Patent [19]

Hamer et al.

[11] Patent Number: 5,006,563

[45] Date of Patent: Apr. 9, 1991

[54] ALKYLAMINO- AND ALKYLAMINO ALKYL DIARYLKETONES

[75] Inventors: R. Richard L. Hamer, Lebanon; Brian Freed, Somerset; Richard C. Allen, Flemington, all of N.J.

[73] Assignee: Hoechst-Roussel Pharmaceuticals Inc., Somerville, N.J.

[21] Appl. No.: 561,202

[22] Filed: Jul. 31, 1990

Related U.S. Application Data

[63] Continuation of Ser. No. 450,502, Dec. 14, 1989, abandoned.

[51] Int. Cl.$^5$ .................. A61K 31/135; C07C 211/27; C07C 211/46; C07C 215/74
[52] U.S. Cl. ................... 514/646; 514/655; 564/305; 564/384; 564/389; 564/441; 564/442; 564/443
[58] Field of Search ............... 564/305, 384, 389, 441, 564/442, 443; 514/646, 655

[56] References Cited

U.S. PATENT DOCUMENTS

| | | | |
|---|---|---|---|
| 3,077,470 | 2/1963 | Burckhalter | 564/384 |
| 3,839,361 | 10/1974 | Terayama et al. | 564/384 |
| 3,957,777 | 5/1976 | Toth et al. | 564/384 |
| 3,996,279 | 12/1976 | Schlager | 564/389 |
| 4,245,099 | 1/1981 | Itoh et al. | 546/315 |
| 4,273,785 | 6/1981 | Shepard | 514/646 |

FOREIGN PATENT DOCUMENTS

| | | | |
|---|---|---|---|
| 0203048 | 12/1982 | Japan | 514/646 |
| 60-11401 | 1/1985 | Japan | |
| 60-11452 | 1/1985 | Japan | |
| 2026480 | 2/1980 | United Kingdom | 546/315 |

OTHER PUBLICATIONS

Dafforn et al., *Biochemical and Biophysical Research Communications*, 104, No. 2, 597-602 (1982).
Buck et al., *J. Chem. Soc.*, 52, 4107 (1930).
Brodbeck et al., *Biochemica et Biophysica Acta*, 567, 357-369 (1979).
Gelb et al., *Biochemistry*, 24, No. 8, 1813-1817 (1985).
Yamada et al., "Thermal Rearrangement of Optically Active, etc.", CA, 68, p. 1147, #12198n, 1968.

*Primary Examiner*—Glennon H. Hollrah
*Attorney, Agent, or Firm*—Raymond R. Wittekind

[57] ABSTRACT

This invention relates to alkylamino and alkyl amino alkyl diarylketones of the formula

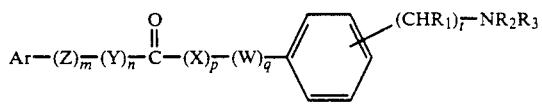

where Ar is aryl of the formula

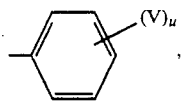

where V is hydrogen, halogen, loweralkyl, loweralkoxy, $CF_3$, $NO_2$ and u is an integer of 1 to 3; X and Y are independently $CH_2$—, —$CH_2$— or —CHF—; Z and W are independently —$CH_2$—, —O—, —CHOH—, or —CHF—; m, n, p, q and t are integers which are independently 0 or 1; $R_1$ is H or loweralkyl; $R_2$ and $R_3$ are loweralkyl; and the pharmaceutically acceptable acid addition salts thereof and where applicable the geometric and optical isomers and racemic mixtures thereof. The compounds of this invention display utility as analgesic agents and as agents for alleviating various memory dysfunctions, characterized by a decreased cholinergic function, such as Alzheimer's disease.

23 Claims, No Drawings

ALKYLAMINO- AND ALKYLAMINO ALKYL DIARYLKETONES

This is a continuation of co-pending application Ser. No. 07/450,502 filed on Dec. 14, 1989, abandoned.

This invention relates to alkylamino and alkyl amino alkyl diarylketones of the formula

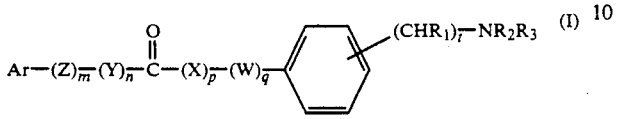

where Ar is aryl of the formula

where V is hydrogen, halogen, loweralkyl, loweralkoxy, $CF_3$, and $NO_2$ and u is an integer of 1 to 3; X and Y are independently $CH_2-$, $-CF_2-$ or $-CHF-$; Z and W are independently $-CH_2-$, $-O-$, $-CHOH-$, or $-CHF-$; m, n, p, q and t are integers which are independently 0 or 1; $R_1$ is H or loweralkyl; $R_2$ and $R_3$ are loweralkyl; and the pharmaceutically acceptable acid addition salts thereof and where applicable the geometric and optical isomers and racemic mixtures thereof.

In a preferred embodiment the invention is related to compounds of Formula I where V is elected from the group H or Cl, u is 1, t is O, and $R_2$, $R_3$ are methyl, Throughout the specification and appended claims, a given chemical formula or name shall encompass all geometric and stereoisomers and racemic mixtures where such isomers and mixtures exist.

In the above definitions, the term "lower" means the group it is describing contains from 1 to 6 carbon atoms. The term "alkyl" refers to a straight or branched chain hydrocarbon containing no unsaturation, e.g. methyl, ethyl, propyl, isopropyl, 2-butyl, neopentyl, n-hexyl, etc.; the term "alkoxy" refers to a monovalent subsituent which consists of an alkyl group linked through an ether oxygen having its free valence bond from the ether oxygen, e.g. methoxy, ethoxy, propoxy, butoxy, pentoxy, etc.; the term "halogen" refers to a member of the halogen family consisting of fluorine, chlorine, bromine and iodine.

The compounds of the present invention are prepared in the following manner. The substituents Ar, Z, Y, X, W, $R_1$ through $R_3$ and the numbers m, n, p, q, t are as defined above unless indicated otherwise.

1. ORGANOMETALLIC METHODS

A. A halide of the formula $Ar-(Z)_m-(Y)_n-Hal$ (II), where Hal is a halogen selected from Cl, Br, and I is selected. Such halides are commerically available or can be synthesized by conventional techniques well known by one of ordinary skill in the art. Compound II is reacted with a metal, e.g. Mg, under conventional Girgnard reagent formation reaction conditions, such as in an ethereal solvent, e.g. ether, tetrahydrofuran, 1,2-dimethoxyethane, etc., at room temperature to reflux for 60 to 90 minutes to form Grignard reagent II of the formula

Compound III in turn is reacted with a compound of the formula

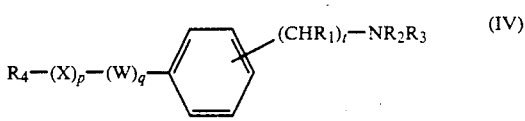

where $R_4$ is a carboxylic acid derivative, such as for example,

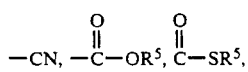

where $R_5$ is loweralkyl;

etc. Compound IV is well known or can be synthesized by conventional techniques well known by one of ordinary skill in the art. Compound III and Compound IV are reacted under conventional Grignard reaction conditions well known in the art, such as in an ethereal solvent, e.g. ether, tetrahydrofuran, 1,2-dimethoxyethane, etc., at a temperature of 0 to reflux for one half to 18 hours to form Compound I.

B. In an alternative embodiment a halide of the formula

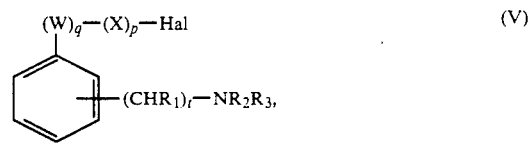

where Hal is a halogen selected from Cl, Br, I, is reacted with a metal, e.g. Mg, under conventional Grignard reaction conditions and then the resultant Grignard reagent is reacted with Compound VI of the formula

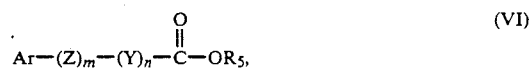

where $R_5$ is loweralkyl, to give Compound I.

C. Alternatively, where q and p are 0, Compound V is reacted with a lithium reagent, e.g. tertiary-butyl lithium, n-butyl lithium, sec-butyl lithium, etc. under conventional lithiation reaction conditions to form a compound having the formula

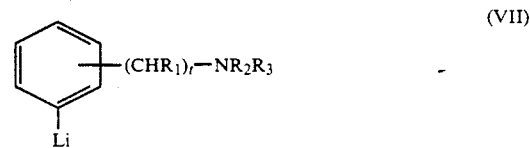

Typically, this reaction is carried out in an ethereal solvent, e.g. ether, tetrahydrofuran, etc., at a temperature of $-78°$ to $0°$ C. for 1 to 2 hours. Compound VII in turn is reacted with Compound VI, under conventional organometallic reaction conditions to form Compound I. Typically this reaction is carried out in an ethereal solvent, e.g. ether, tetrahydrofuran, etc., at a temperature of −78° to 20° C. for 15 to 60 minutes.

2. BENZOIN CONDENSATION

A. An aldehyde of the formula

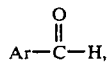

(VIII)

is reacted with a second aldehyde of the formula

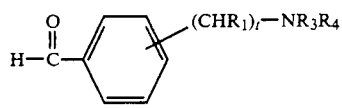

(IX)

under conventional benzoin condensation reaction conditions to form Compound X of the invention of the formula

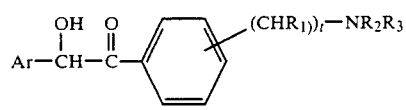

(X)

Typically the reaction is carried out in a manner taught by Johannes S. Buck et al., *J. Chem. Soc.*, 52, 220 (1930).

B. Compound X may be subjected to conventional reduction by means of a suitable reducing agent, e.g. tin, zinc, etc., in a protic solvent, e.g. methanol, ethanol, etc., in the presence of a mineral acid, e.g. hydrochloric, hydrobromic, etc., at a temperature of 20° C. to reflux for 2 to 4 hours to form Compound XI of the invention having the formula

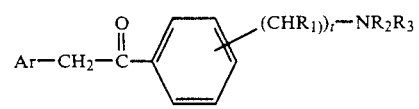

(XI)

C. Alternatively, Compound X is reacted with diethylaminosulfurtrifluoride in a chlorinated solvent, e.g. dichloromethane, chloroform, 1,2-dichloroethane, etc., at a temperature of −78° to 20° C. for 24 to 48 hours to form Compound XII of the invention having the formula

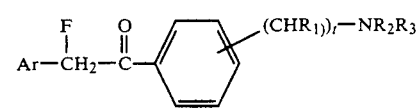

(XII)

3. TOSYLMETHYL ISOCYANIDE SYNTHESIS

Employing the procedure of van Leusen et al., *Tetrahedron Letters*, No. 48, pp. 4229–4232 (1977), Compound I of the invention can be obtained. Compound II and V are reacted with tosylmethyl isocyanide to form Compound I. Typically, the reaction is carried out in the presence of a strong base, e.g. sodium hydroxide, potassium hydroxide etc., initially for 30 to 90 minutes at a temperature of 0° to 25° C. and then in the presence of an acidic solvent, e.g. ethereal hydrogen chloride, ethereal hydrogen bromide, etc. at a temperature of 0° to 25° C. for 5 to 30 minutes to form Compound I.

4. WILLIAMSON SYNTHESIS

A. Utilizing the procedure taught in Suzuki et al., *J. Pharm. Soc. Japan*, 75, 54 (1955) a compound of the formula

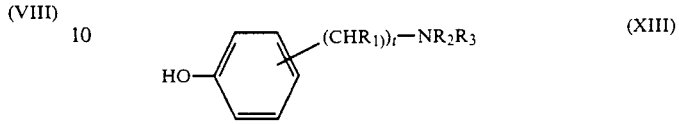

(XIII)

is reacted in the presence of a base, e.g. potassium carbonate, sodium bicarbonate, etc., with a compound of the formula,

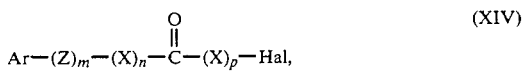

(XIV)

where Hal is a halogen selected from Cl, Br, I, in a dipolar aprotic solvent, e.g. methyl ethyl ketone, dimethylformamide, acetonitrile, etc., at a temperature of 20° to 80° C. for 6 to 36 hours to form Compound XV of the invention having the formula,

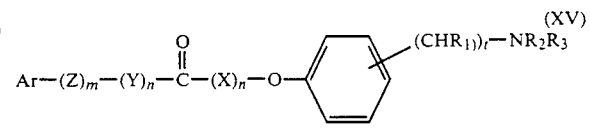

(XV)

B. Alternatively, a phenol of the formula Ar—OH, (XVI), in the presence of a base, is reacted, as described above in 4A, with Compound XVII of the formula

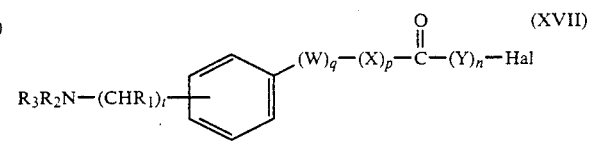

(XVII)

where Hal is a halogen selected from Cl, Br, and I, to form Compound XVIII of the invention having the formula

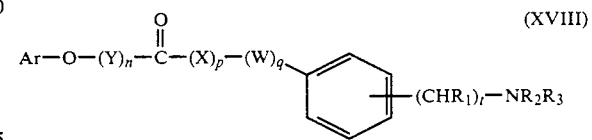

(XVIII)

5. REFORMATSKII

A. A Compound of the formula

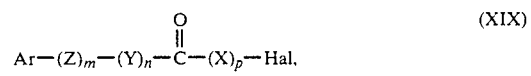

(XIX)

where Hal is a halogen selected from Cl, Br and I, is selected. Compound XIX is reacted in the presence of activated zinc under typical Reformatskii reaction conditions with Compound XX having the formula

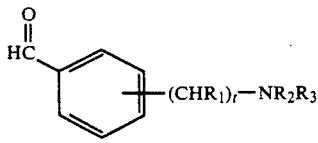

in a solvent, e.g., dimethylformamide, tetrahydrofuran, etc. at a temperature of 20° to 80° C. for 18 to 24 hours to form Compound XXI of the invention having the formula

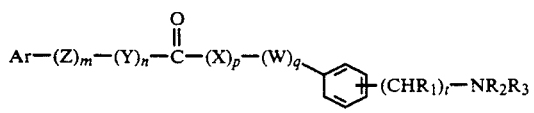

where q is 1 and W is CHOH.

B. Alternatively, a benzaldehyde of the formula

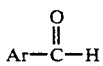

is reacted with a compound (XXIII) of the formula

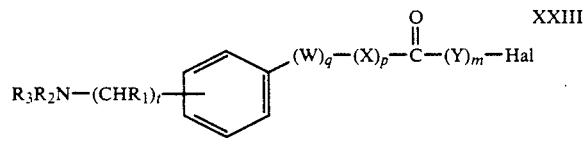

, where Hal is as defined above, under Reformatskii reaction conditions, as described above in 5A, to give Compound I of the invention (where m is 1 and Z is CHOH).

Alternatively, Compound XXI, where m and q are 1 and Z and W are independently CHOH, is treated with diethylaminosulfurtifluoride as described above in 2C to give Compound I where m and q are 1 and Z and W are independently CHF.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesic activity [Proc. Soc. Exptl. Biol. Med. 95, 729 (1957)]. The analgesic activity of some of the compounds expressed in terms of percent inhibition of writhing are given in TABLE I.

TABLE 1

| Compound | Dose (subcutaneous) (mg/kg of body wt.) | Inhibition in Writhing (%) |
| --- | --- | --- |
| 1-(3-chlorophenyl)-3-[3-(dimethylamino)-phenoxy]-2-propanone | 20 | 41 |
| 2-(3-chlorophenyl)-2,2-difluoro-1-[3-dimethylamino)-phenyl]ethanone hydrochloride | 20 | 50 |
| 2,2-difluoro-1-[4-(dimethyl-amino)phenyl]-2-phenylethanone | 20 | 67 |
| 2-[3-(chlorophenyl)-2-fluoro-1-[4-(dimethylamino)phenyl]-ethanone | 20 | 44 |
| 2-(3-chlorophenoxy)-1-[3-(dimethylamino)phenyl]-ethanone | 20 | 69 |
| 1-(3-chlorophenyl)-3-[(3-dimethylamino)phenyl]-2-propanone | 20 | 51 |
| 3-(3-chlorophenyl)-2,2-difluoro-3-hydroxy-1-[3-(dimethylamino)phenyl]-propanone hydrochloride | 20 | 63 |
| 1,1-difluoro-3-[3-(dimethylamino)phenyl]-1 phenyl-2-propanone | 20 | 58 |
| propoxyphene (standard) | 3.9 | 50 |

The analgesic relief of pain is achieved when the compounds of the invention are administered to a subject requiring such treatment at an effective oral, parenteral or intravenous dose of from 0.1 to 25 mg/kg of body weight per day. A preferred effective dose within this range is from 1 to 10 mg/kg of body weight per day. A particularly preferred effective amount is about 2 mg/kg of body weight per day. It is to be understood, however, that for any particular subject, specific dosage regimens should be adjusted according to the individual need. It is further to be understood that the dosages set forth herein are examples only and that they do not to any extent, limit the scope of practice of the invention.

The compounds of the present invention can also be used for the treatment of various memory dysfunctions characterized by decreased cholinergic function such as Alzheimer's disease.

The utility can be ascertained by determining the ability of these compounds to inhibit the activity of the enzyme acetylcholinesterase and thereby increase the acetylcholine levels in the brain.

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandesent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 2.

TABLE 2

| Compound | Dose mg/kg,s.c. | Dark Avoidance Assay<br>% of animals with scopolamine induced memory deficit reversal |
|---|---|---|
| 2-(3-chlorophenyl)-1-[3-(dimethylamino)-phenyl]ethanone hydrochloride | 0.16 | 40 |
| physostigmine (reference) | 0.31 | 20 |

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% alkylamino- and alkylaminoalkyl diarylketones of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the alkylamino- and alkylaminoalkyl diarylketones of the present invention.

The tablets, pills, capsules, troches and the like may also contain the following ingredients: a binder such as microcystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as collodial silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the compounds of the present invention may be incorporated into a solution or suspension. These preparations should contain at least 0.1% of the alkylamino- and alkylaminoalkyl diarylketones derivative of the invention, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 milligrams of the alkylamino- and alkylaminoalkyl diarylketones derivative of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Examples of some of the compounds include:

2-(3-fluorophenyl)-1-[3-dimethylamino)phenyl]ethanone;

2-(3-iodophenyl)-1-[3-dimethylamino)phenyl]ethanone;

2-(3-trifluorophenyl)-1-[3-dimethylamino)phenyl]ethanone;

2-(3-methylphenyl)-1-[3-dimethylamino)phenyl)]ethanone;

2-(2-chlorophenyl)-1-[3-(dimethylamino)phenyl]ethanone;

2-(3,4-dichlorophenyl)-1-[3-(diethylamino)phenyl]ethanone;

2-(3-chlorophenyl)-1-[3-(N-ethyl-N-methylamino)-phenyl]ehtanone;

2,2-difluoro-1-[2-(dimethylamino)phenyl]-2-phenylethanone;

2,2-difluoro-1-[4-(dimethylamino)phenyl]-2-(3-methoxyphenyl)ethanone;

2,2-difluoro-1-[4-(dimethylamino)phenyl]-2-(3-chlorophenyl)ehtanone;

2-(3-nitrophenoxy)-1-[3-dimethylamino)phenyl]ethanone;

2-(3-(trifluoromethyl)phenoxy)-1-[3-dimethylamino)-phenyl]ethanone;

2-(2,3-dichlorophenoxy)-1-[3-(dimethylamino)phenyl]ethanone;

3-(3-chlorophenyl)-2,2,3-trifluoro-1-[3-(dimethylamino)phenyl]propanone;

2-(3-chlorophenoxy)-2,2-difluoro-1-[3-(dimethylamino)phenyl]ethanone.

The following examples are for illustrative purposes and are not to be construed as limiting the invention disclosed herein.

The temperatures are given in degrees centigrade unless indicated otherwise.

EXAMPLE 1

2-(3-chlorophenyl)-1-[3-[(dimethylamino)methyl]-phenyl]ethanone hydrochloride

A solution of 5.50 g of 3-chlorobenzyl bromide in 100 ml of dry ether was added slowly to 0.98 g of magnesium in 150 ml of dry ether under nitrogen. The Grignard reagent was stirred at ambient temperature for one hour and then added to a solution of 2.86 g of 3-[(dimethylamino)methyl]benzonitrile in 150 ml of dry ether. The resulting slurry was stirred at room temperature overnight and then quenched with the dropwise addition of saturated ammonium chloride solution. This was diluted with water and the layers separated. The aqueous phase was extracted with ethyl acetate and the combined organic extracts were dried ($Na_2SO_4$), filtered, and evaporated. The residue was purified by flash chromatography (silica gel; ethyl acetate) and then treated with ethereal HCl until acidic to wet litmus paper. The precipitate was collected and recrystallized from ethanol-ether to give 2.2 g of 2-(3-chlorophenyl)-1-[3-[(dimethylamino)methyl]phenyl]ethanone hydrochloride, m.p. 187°–189° C.

ANALYSIS: Calculated for $C_{17}H_{18}ClNO \cdot HCl$: 62.97% C, 5.91% H, 4.32% N, Found: 62.92% C, 5.97% H, 4.35% N.

EXAMPLE 2

2-(3-Chlorophenyl)-1-[3-(dimethylamino)phenyl]ethanone hydrochloride

A solution of 10.0 g of 3-chlorobenzyl chloride in 100 ml of dry ether was added slowly to 2.26 g of magnesium in 75 ml of dry ether under nitrogen. The Grignard reagent was stirred at ambient temperature for one hour and then added to a solution of 4.5 g of 3-dimethylaminobenzonitrile in 150 ml of dry ether. After the addition a catalytic amount of CuBr was added and the solution stirred overnight. The reaction was quenched with 200 ml of ammonium chloride solution and diluted with water. The layers were separated and the aqueous phase extracted with ethyl acetate. The combined organic layers were dried ($Na_2SO_4$), filtered and evaporated. The residue was purified by flash chromatography (silica gel: 8:1 hexane-ethyl acetate) and then treated with ethereal HCl until acidic to wet litmus paper. The precipitate was collected and recrystallized from ethanol-ether to give 3.8 g of 2-(3-chlorophenyl)1-[3-(dimethylamino)phenyl]ethanone hydrochloride, m.p. 92°-94° C.

ANALYSIS: Calculated for $C_{16}H_{16}ClNO \cdot HCl$: 61.95% C, 5.52% H, 4.51% N, Found: 62.14% C, 5.58% H, 4.57% N.

EXAMPLE 3

1-(3-Chlorophenyl)-3-[3-(dimethylamino)phenoxy]-2-propanone

A solution of 10.0 g of 3-chlorobenzyl chloride in 75 ml of dry ether was added slowly to 2.25 g of magnesium powder in 75 ml of dry ether under nitrogen. The Grignard reagent was stirred at ambient temperature for one hour and then added to a solution of 5.47 g of 3-(dimethylamino)phenoxyacetonitrile in 200 ml of dry ether stirred at 0° C. The reaction was warmed to room temperature overnight and then quenched with of $NH_4Cl$ solution. The mixture was diluted with of water and the layers separated. The aqueous phase was extracted with ethyl acetate and the combined organic extracts were dried ($Na_2SO_4$), filtered, and evaporated. The residue was purified by flash chromatography (silica gel; 8:1 hexane-ethyl acetate) and recrystallized from ethyl acetate-hexane to give 4.3 g of 1-(3-chlorophenyl)-3-[3-dimethylamino)phenoxy]-2-propanone, m.p. 82°-83° C.

ANALYSIS: Calculated for $C_{17}H_{18}ClNO_2$: 67.21% C, 5.97% H, 4.61% N, Found: 67.10% C, 5.93% H, 4.60% N.

EXAMPLE 4

2,2-Difluoro-1-[4-(dimethylamino)phenyl]-2-phenylethanone

A solution of 4.0 g of 4-bromo-N,N-dimethylaniline in 50 ml of dry tetrahydrofuran at −78° C. was treated with 23.5 ml of 1.7M tert-butyllithium in pentane under nitrogen over 5 minutes with rapid stirring. After 0.5 hour, the slurry was warmed to −30° C. and added to a solution of 4.0 g of α,α-difluorophenylacetate in 50 ml of dry tetrahydrofuran at −78° C. After 1 hour at −78° C., the solution was allowed to warm to room temperature and stirred overnight. The solution was poured into water and extracted with ethyl acetate. Evaporation left a solid which was purified by flash chromatography (1:1 ethyl acetate-hexane) to give a powder. Recrystallization from ethyl acetate-hexane gave 1.75 g of 2,2-difluoro-1-[4-(dimethylamino)phenyl]-2-phenylethanone, m.p. 115°-116° C.

ANALYSIS: Calculated for $C_{16}H_{15}F_2NO$: 69.81% C, 5.49% H, 5.09% N, Found: 69.77% C, 5.49% H, 5.12% N.

EXAMPLE 5

2-(3-Chlorophenyl)-2,2-difluro-1-[4-(dimethylamino)phenyl]ethanone

A solution of 4.2 g of 4-bromo-N,N-dimethylaniline in 50 ml of dry ether was treated with 9.2 ml of a 2.5M solution of n-butyllithium in hexane under nitrogen and stirred at room temperature for 2 hours. This solution was cooled to −78° C. and added to a solution of 5.4 g of ethyl α,α-difluro(3-chlorophenyl)acetate in 50 ml of dry ether at −115° C. After 2 hours the solution was syringed into water and extracted with ether. Evaporation left a gummy residue which was purified by flash chromatography (silica gel, 10:1 hexane-ethyl acetate) to give 2.1 g of a powder. Recrystallization from hexane-ethyl acetate affords 1.7 g of 2-(3-chlorophenyl)-2,2-difluoro-1-[4(dimethylamino)phenyl]ethanone, m.p. 104°-108° C.

ANALYSIS: Calculated for $C_{16}H_{14}ClF_2NO$: 62.04% C, 4.56% H, 4.52% N, Found: 62.23% C, 4.56% H, 4.45% N.

EXAMPLE 6

2-(3-Chlorophenyl)-2,2-difluoro-1-[3-(dimethylamino)phenyl]ethanone hydrochloride A solution of 3.0 g of 3-bromo-N,N-dimethylaniline in 60 ml of dry tetrahydrofuran (THF) was cooled to −78° C. and treated with 17.6 ml of a 1.7M solution of tert-butyllithium in pentane under nitrogen. After 1 hour at −78° C., this slurry was added to a solution of 3.5 g of ethyl α,α-difluoro(3-chlorophenyl)acetate in 50 ml of dry THF and stirred at −78° C. for 1.5 hours. The reaction was quenched by pouring into water and was extracted with ethyl acetate. The combined extracts were evaporated and the residue purified by HPLC [18:1 hexane-ethyl acetate] to give 3.7 g of a oil. This oil was treated with ethereal HCl and the precipitate was recrystallized first from ethyl acetate and then THF-ether to give 1.48 g of 2-(3-chlorophenyl)-2,2-(difluoro-1-[3-(dimethylamino)phenyl]ethanone hydrochloride, m.p. 104°-106° C.

ANALYSIS: Calculated for $C_{16}H_{14}ClF_2NO \cdot HCl$: 55.51% C, 4.37% H, 4.05% N, Found: 55.44% C, 4.48% H, 3.98% N.

EXAMPLE 7

1,1-Difluoro-3-[3-(dimethylamino)phenyl-1-phenyl-2-propanone

A solution of 12.1 g of m-dimethyltoluidine and 10.4 g of tetramethylene diamine was treated with 36 mL of a 2.5M solution of n-butyl lithium in hexane under nitrogen and stirred at 45° C. for 1.5 hours. This solution was added to a solution of 18.0 g of ethyl α,α-difluorophenyl) acetate in 150 mL of dry tetrahydrofuran at −78° C. After 2 hours at −78° C., this solution was poured into saturated sodium bicarbonate solution and extracted with ethyl acetate. Evaporation left an oil which was purified by HPLC (7:1 hexane-dichloromethane) to give 6.3 g of an oil that crystallized on standing. Recrystallization from ether-pentane yielded 4.2 g of 1,1-difluoro-3-[3-(dimethylamino)phenyl]-1-phenyl-2-propanone, mp 76°-77° C.

ANALYSIS: Calculated for $C_{17}H_{17}F_2NO$: 70.57% C, 5.92% H, 4.84% N, Found: 70.39% C, 5.96% H, 4.75% N.

EXAMPLE 8

1-(3-Chlorophenyl)-3-[3-(dimethylamino)phenyl]-2-propanone

A rapidly stirred mixture of 100 mL of 40% aqueous sodium hydroxide, 1.2 g of tetrabutylammonium iodide, 12.9 g of tosylmethyl isocyanide and 120 mL of dichloromethane was treated with 19.5 g of solid 3-(dimethylamino)benzyl bromide hydrobromide. After 30 minutes, 15 g of 3-chlorobenzyl bromide was added and the mixture stirred at ambient temperature for 2 hours then separated. The aqueous phase was neutralized and extracted with dichloromethane. The combined extracts were evaporated and the residue purified by high performance liquid chromatography (dichloromethane) to give 5.4 g of a powder. This powder was suspended in 25 mL of ether and 10 mL of dichloromethane and treated with 2 mL of concentrated HCl. This mixture was swirled for 5 minutes, neutralized, and extracted with dichloromethane. Evaporation gave an oil that was purified by flash chromatography (dichloromethane) to give 2.3 g of a powder. Recrystallization from ether-hexane gave 1.7 g of 1-(3-chlorophenyl)-3-[3-(dimethylamino)phenyl]-2-propanone, mp 58°-60° C.

ANALYSIS: Calculated for $C_{17}H_{18}ClNO$: 70.95% C, 6.30% H, 4.87% N, Found: 70.80% C, 6.40% H, 4.75% N.

EXAMPLE 9

1-(3-Chlorophenyl)-2-[3-(dimethylamino)phenoxy]ethanone

A slurry of 3.0 g of 3-dimethylaminophenol, 6.05 g of milled potassium carbonate and 75 ml of acetone was stirred at room temperature under nitrogen for 30 minutes and then a solution of 7.66 g of α-bromo-3-chloroacetophenone in 75 ml of acetone was added dropwise. The slurry was stirred at room temperature for 72 hours. Filtration and evaporation gave a residue which was purified by high performance liquid chromatography (7:1 hexane-ethyl acetate). The resulting solid was recrystallized from ethyl acetate-hexane to give 3.0 g of 1-(3-chlorophenyl)-2-[3-(dimethylamino)phenoxy]ethanone, m.p. 101°-103° C.

ANALYSIS: Calculated for $C_{16}H_{16}ClNO_2$: 66.32% C, 5.57% H, 4.83% N, Found: 66.33% C, 5.49% H, 4.81% N.

EXAMPLE 10

1-(3-Chlorophenyl)-2-[4-(dimethylamino)phenoxy]ethanone

A slurry containing 3.5 g of 4-dimethylaminophenol hydrochloride and 6.9 g of milled potassium carbonate in 100 mL of 2-butanone was treated with a solution of 7.0 g of 3-chloro-α-bromoacetophenone in 75 mL of 2-butanone and the whole stirred at room temperature overnight. The reaction mixture was quenched with of saturated sodium bicarbonate solution and extracted with dichloromethane. The extracts were dried (MgSO₄), filtered and evaporated to an oil. This oil was purified by high performance liquid chromatography (7:3 hexane-ethyl acetate) to give a solid. Recrystallization from ether-hexane gave 0.90 g of 1-(3-chlorophenyl)-2-[4-(dimethylamino)phenoxy]ethanone, mp 69°-70° C.

ANALYSIS: Calculated for $C_{16}H_{16}ClNO_2$: 66.33% C, 5.57% H, 4.83% N, Found: 66.14% C, 5.51% H, 4.71% N.

EXAMPLE 11

2-(3-Chlorophenoxy)-1-[3-(dimethylamino)phenyl]ethanone

A stirred slurry containing 4.24 g of 3-chlorophenol and 6.9 g of milled potassium carbonate in 150 mL of dry 2-butanone was treated with a solution of 8.03 g of 3-dimethylamino-α-bromoacetophenone in 60 mL of dry 2-butanone. This mixture was stirred at 40° C. under nitrogen overnight then evaporated. This mass was taken up in dichloromethane, filtered and concentrated. The residue was purified by high performance liquid chromatography (dichloromethane) to give an oil that crystallized on standing. Recrystallization from ether gave 4.4 g of 2-(3-chlorophenoxy)-1-[3-(dimethylamino)phenyl]ethanone, mp 70°-72° C.

ANALYSIS: Calculated for $C_{16}H_{16}ClNO_2$: 66.32% C, 5.57% H, 4.83% N, Found: 66.18% C, 5.31% H, 4.76% N.

EXAMPLE 12

2,3'-Dichloro-2,2-difluoroacetophenone

A solution of 25 g of 3-bromochlorobenzene in 100 ml ether was added to a solution of 15.1 g of tetramethylenediamine, 52.4 ml of a 2.5M solution of n-butyllithium in hexane and 75 ml ether at −78° C. under nitrogen. After 1 hour, a solution of 31.0 g of ethyl chlorodifluoroacetate in 150 ml ether was added. After warming to room temperature, the reaction was poured into excess ammonium chloride solution and extracted with ether. The extracts were dried (Na₂SO₄) and evaporated. The residue was distilled (0.1 mm Hg) to give 14.7 g of an oil which was used directly.

1-(3-Chlorophenyl)-2,2-difluoro-3-hydroxy-3-[3-(dimethylamino)phenyl]propanone

A solution of 9.3 g of 2,3'-dichloro-2,2-difluoroacetophenone and 6.8 g of 3-dimethylaminobenzaldehyde in 50 ml of dry dimethylformamide was stirred at 0° C. as 4.0 g of activated zinc was added in small portions under nitrogen. The mixture was stirred overnight with gradual warming to room temperature. The reaction was quenched with aqueous NH₄Cl solution and the product was extracted with ethyl acetate. The combined organic extracts were dried (Na₂SO₄), filtered, and evaporated. The residue was purified by high performance liquid chromatography (5:1 hexane-ethyl acetate) and then recrystallized from ether-hexane to give 1.7 g of 1-(3-chlorophenyl)-2,2-difluoro-3-hydroxy-3-[3-(dimethylamino)phenyl]-propanone, m.p. 105°-106° C.

ANALYSIS: Calculated for $C_{17}H_{16}ClF_2NO_2$: 60.10% C, 4.75% H, 4.12% N, Found: 60.13% C, 4.88% H, 4.05% N.

EXAMPLE 13

3-(3-Chlorophenyl)-2,2-difluoro-3-hydroxy-1-[3-(dimethylamino)phenyl]propanone hydrochloride A solution of 6.3 g of 3-chlorobenzaldehyde and 9.5 g of 2-chloro-2,2-difluoro-3'-(dimethylamino)acetophenone in 75 ml of dry dimethylformamide was stirred at 0° C. as 4.0 g of activated zinc was added in small portions under nitrogen. The mixture was stirred overnight with gradual warming to room temperature. The reaction was quenched with aqueous NH₄Cl solution and the product was extracted with ethyl acetate. The combined organic extracts were dried (Na₂SO₄), filtered, and evaporated. The residue was purified by high perforamnce liquid chromatography (5:1 hexane-ethyl acetate) and the resulting oil was treated with ethereal HCl. The salt was collected and recrystallized from ethyl acetate to give 1.9 g of 3-(3-chlorophenyl)-2,2-difluoro-3-hydroxy-1-[3-(dimethylamino)phenyl]propanone hydrochloride, m.p. 140°–142° C.

ANALYSIS: Calculated for $C_{17}H_{17}Cl_2F_2NO_2$: 54.27% C, 4.55% H, 3.72% N, Found: 54.23% C, 4.49% H, 3.65% N.

EXAMPLE 14

Ethyl 3-(3-chlorophenyl)-2,2,3-trifluoropropionate

A solution of 25 g of ethyl 3-(3-chlorophenyl)-3-hydroxy-2,2-difluoropropionate in 140 mL $CH_2Cl_2$ was treated with a solution of 14 g of diethylaminosulfurtrifluoride in 10 mL $CH_2Cl_2$ at room temperature. After 3 hours, the mixture was poured into aqueous NaHCO₃, extracted with ethyl acetate, dried (Na₂SO₄) and evaporated. The residue was distilled (0.1 mm Hg) to give 18.7 g of an oil which was used directly.

3-(3-Chlorophenyl)-2,2,3-trifluoro-1-[3-(dimethylamino)phenyl]propanone hydrochloride A solution of n-butyllithium (25.2 ml of 2.5M in hexanes) and 7.33 g of tetramethylenediamine in 100 ml of dry ether was stirred at −78° C. under nitrogen as a solution of 12.6 g of 3-bromo-N,N-dimethylaniline in 75 ml of dry ether was added dropwise. The reaction was stirred at −78° C. for 2 hours and then was added to a solution of 18.5 g of ethyl 3-(3-chlorophenyl)-2,2,3-trifluoropropionate in 150 mL ether at −78° C. After stirring at −78° C. for one hour, the reaction was warmed to room temperature. The reaction was then quenched with aqueous NH₄Cl solution and basified with dilute K₂CO₃ solution. The layers were separated and the aqueous phase extracted with ethyl acetate. The combined organic layers were dried (Na₂SO₄), filtered, and evaporated. The residue was purified by high performance liquid chromatography [12:1 hexane-ethyl acetate] to give 15.1 g of an oil. This material was treated with ethereal HCl and the solid was collected and recrystallized from ethyl acetate to give 9.3 g of 3-(3-chlorophenyl)-2,2,3-trifluoro-1-[3-(dimethylamino)phenyl]propanone hydrochloride, m.p. 138°–140° C.

ANALYSIS: Calculated for: 53.99% C, 4.26% H, 3.70% N, Found: 54.71% C, 4.25% H, 3.73% N.

EXAMPLE 15

1-Chloro-1,1-difluoro-3-phenylacetone

A solution of 20 g of ethyl chlorodifluoroacetate in 150 ml ether was treated with one equivalent of benzyl magnesium chloride in 63 ml THF at −40° C. under nitrogen. After 2 hours, the reaction was poured into aqueous NH₄Cl and extracted with ether. Evaporation and distillation (0.1 mm Hg) of the residue gave 24.8 g of an oil which was used directly.

3,3-Difluoro-4-hydroxy-4-[3-(dimethylamino)phenyl]-1-phenyl-2-butanone hydrochloride A solution of 20 g of 1-chloro-1,1-difluoro-3-phenylacetone and 13.3 g of 3-dimethylaminobenzaldehyde in 35 ml of dry dimethylformamide was stirred at room temperature under nitrogen as 8.7 g of as activated zinc was added in three portions. The slurry was heated to 60° C. and stirred overnight. The reaction was quenched with NH₄Cl solution, basified with K₂CO₃ solution, and extracted with ethyl acetate. The combined organic layers were dried (Na₂SO₄), filtered, and evaporated. The residue was purified by high performance liquid chromatography (6:1 hexane-ethyl acetate) to give 6.2 g of an oil. This material was treated with ethereal HCl and the solid was collected and recrystallized from ethyl acetate to give 4.3 g of 3,3-difluoro-4-hydroxy-4-[3-(dimethylamino)phenyl]-1-phenyl-2-butanone hydrochloride, m.p. 159°–161° C.

ANALYSIS: Calculated for: 60.76% C, 5.67% H, 3.94% N, Found: 60.71% C, 5.86% H, 3.91% N.

EXAMPLE 16

2-(3-Chlorophenyl)-1-[4-(dimethylamino)phenyl]ethanone

A mixture of 9.08 g, of 2-(3-chlorophenyl)-2-hydroxy-1-[4-(dimethylamino)phenyl]ethanone, 3 equivalents of mossy tin, a spatula tip of copper (II) sulfate, 20 ml of concentrated HCl, and 60 ml of 95% ethanol was stirred at reflux 3 hours. The mixture was basified with potassium carbonate solution and filtered. The cake was washed with ethyl acetate and the filtrate separated. The aqueous phase was extracted with ethyl acetate and the combined organic layers were dried (Na₂SO₄), filtered, and evaporated. The residue was purified by flash chromatography (10:1 hexane-ethyl acetate) and then recrystallized from ethyl acetate-hexane to give 3.8 g of 2-(3-chlorophenyl)-1-[4-(dimethylamino)phenyl]ethanone, m.p. 126°–128° C.

ANALYSIS: Calculated for $C_{16}H_{16}ClNO$: 70.20% C, 5.89% H, 5.12% N, Found: 70.35% C, 5.98% H, 5.06% N.

EXAMPLE 17

2-(3-Chlorophenyl)-2-fluoro-1-[4-(dimethylamino)phenyl]ethanone

A solution 6.7 g diethylaminosulfur trifluoride in 20 ml of dry dichloromethane was stirred at −78° C. under nitrogen as a solution of 12 g of 2-(3-chlorophenyl)-2-hydroxy-1-[4-(dimethylamino)phenyl]ethanone in 200 ml of dry dichloromethane was added dropwise. The mixture was warmed to room temperature and stirred for 72 hours. The mixture was poured into 200 ml of ice water and the layers separated. The organic layer was dried (Na₂SO₄), filtered, and evaporated. The residue was purified by flash chromatography (8:1 hexane-ethyl acetate) and then recrystallized from ether-hexane to give 1.1 g of 2-(3-chlorophenyl)-2-fluoro-1-[4-(dimethylamino)phenyl]ethanone, mp 90°–92° C.

ANALYSIS: Calculated for $C_{16}H_{15}ClFNO$: 65.87% C, 5.18% H, 4.80% N, Found: 65.88% C, 5.16% H, 4.71% N.

We claim:

1. An alkylamino-, alkylaminoalkyl diarylketone of the formula

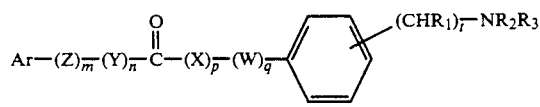

where Ar is aryl of the formula

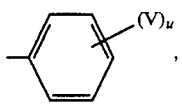

where V is hydrogen, halogen, loweralkyl, loweralkoxy, $CF_3$, $NO_2$ and u is an integer of 1 to 3; X and Y are independently —$CH_2$, —$CF_2$— or —CHF—; Z and W are independently —$CH_2$—, —O—, —CHOH—, or —CHF—; m, n, p, q and t are integers which are independently 0 or 1; $R_1$ is H or loweralkyl, $R_2$ and $R_3$ are loweralkyl; and the pharmaceutically acceptable acid addition salts thereof and where applicable the geometric and optical isomers and racemic mixtures thereof provided that when Z=oxygen n=1, or when W=oxygen p=1, or when both Z and W are simultaneously oxygen, n=p=1 or when W=—CHOH— and m=n=p=t=0 and u=1 then V is neither halogen nor loweralkoxy.

2. The compound as defined in claim 1 which is 2-(3-chlorophenyl)-1-[3-[(dimethylamino)methyl]phenyl]ethanone and the pharmaceutically acceptable acid addition salts thereof.

3. The compound as defined in claim 2 wherein said salt is the hydrochloride.

4. The compound as defined in claim 1 which is 2-(3-chlorophenyl)-1-[3-(dimethylamino)phenyl]ethanone and the pharmaceutically acceptable acid addition salts thereof.

5. The compound as defined in claim 4 wherein said salt is the hydrochloride.

6. The compound as defined in claim 1 which is 1-(3-chlorophenyl)-3-[3-(dimethylamino)phenoxy]-2-propanone and the pharmaceutically acceptable acid addition salts thereof.

7. The compound as defined in claim 1 which is 2,2-difluoro-1-[4-(dimethylamino)phenyl]-2-phenylethanone and the pharmaceutically acceptable acid addition salts thereof.

8. The compound as defined in claim 1 which is 2-(3-chlorophenyl)-2,2-difluoro-1-[4-(dimethylamino)phenyl]ethanone and the pharmaceutically acceptable acid addition salts thereof.

9. The compound as defined in claim 1 which is 2-(3-chlorophenyl)-2,2-difluoro-1-[3-(dimethylamino)phenyl]ethanone and the pharmaceutically acceptable acid addition salts thereof.

10. The compound as defined in claim 9 wherein said salt is the hydrochloride.

11. The compound as defined in claim 1 which is 1,1-difluoro-3-[3-(dimethylamino)phenyl]-1-phenyl-2-propanone and the pharmaceutically acceptable acid addition salts thereof.

12. The compound as defined in claim 1 which is 1-(3-chlorophenyl)-3-[3-(dimethylamino)phenyl]-2-propanone and the pharmaceutically acceptable acid addition salts thereof.

13. The compound as defined in claim 1 which is 2-(3-chlorophenoxy)-1-[3-(dimethylamino)phenyl]ethanone and the pharmaceutically acceptable acid addition salts thereof.

14. The compound as defined in claim 1 which is 1-(3-chlorophenyl)-2,2-difluoro-3-hydroxy-3-[3-(dimethylamino)phenyl]propanone and the pharmaceutically acceptable acid addition salts thereof.

15. The compound as defined in claim 1 which is 3-(3-chlorophenyl)-2,2-difluoro-3-hydroxy-1-[3-(dimethylamino)phenyl]propanone and the pharmaceutically acceptable acid addition salts thereof.

16. The compound as defined in claim 15 wherein said salt is the hydrochloride.

17. The compound as defined in claim 1 which is 3-(3-chlorophenyl)-2,2,3-trifluoro-1-[3-(dimethylamino)phenyl]propanone and the pharmaceutically acceptable acid addition salts thereof.

18. The compound as defined in claim 17 wherein said salt is the hydrochloride.

19. The compound as defined in claim 1 which is 3,3-difluoro-4-hydroxy-4-[3-(dimethylamino)phenyl]-1-phenyl-2-butanone and the pharmaceutically acceptable acid addition salts thereof.

20. The compound is defined in claim 19 wherein said salt is the hydrochloride.

21. The compound as defined in claim 1 which is 2-(3-chlorophenyl)-1-[4-dimethylamino)phenyl]ethanone and the pharmaceutically acceptable acid addition salts thereof.

22. The compound as defined in claim 1 which is 2-(3-chlorophenyl)-2-fluoro-1-[4-(dimethylamino)phenyl]ethanone and the pharmaceutically acceptable acid addition salts thereof.

23. A pharmaceutical composition comprising a compound as defined in claim 1 present in an amount effective for alleviating a memory dysfunction, characterized by decreased cholinergic function, or present in an analgesically effective amount and a suitable carrier therefor.

* * * * *

REEXAMINATION CERTIFICATE (2212th)
United States Patent [19]
Hamer et al.

[11] B1 5,006,563
[45] Certificate Issued  Feb. 8, 1994

[54] ALKYLAMINO AND ALKYLAMINO ALKYL DIARYLKETONES

[75] Inventors: R. Richard L. Hamer, Lebanon; Brian Freed, Somerset; Richard C. Allen, Flemington, all of N.J.

[73] Assignee: Hoechst-Roussel Pharmaceuticals Incorporated, Somerville, N.J.

Reexamination Request:
No. 90/002,401, Aug. 16, 1991

Reexamination Certificate for:
Patent No.: 5,006,563
Issued: Apr. 9, 1991
Appl. No.: 561,202
Filed: Jul. 31, 1990

Related U.S. Application Data

[63] Continuation of Ser. No. 450,502, Dec. 14, 1989, abandoned.

[51] Int. Cl.$^5$ .............. A61K 31/135; C07C 225/10; C07C 225/22
[52] U.S. Cl. .............. 514/646; 514/648; 514/655; 564/305; 564/323; 564/328; 564/384; 564/389; 564/441; 564/442; 564/443
[58] Field of Search .............. 564/305, 323, 328, 384, 564/389, 441, 442, 443; 514/646, 648, 655

[56] References Cited

U.S. PATENT DOCUMENTS

| | | | |
|---|---|---|---|
| 2,223,517 | 12/1940 | Hammond | 564/329 |
| 4,456,671 | 6/1984 | Mabuchi | 430/58 |
| 4,870,095 | 9/1989 | Bailey | 514/406 |

FOREIGN PATENT DOCUMENTS

| | | |
|---|---|---|
| 0308020 | 3/1989 | European Pat. Off. . |
| 139158 | 6/1988 | Japan . |

OTHER PUBLICATIONS

Barnish et al, Journal of Organic Chemistry, vol. 33 (1968) pp. 1372–1374.
DoAmaral et al, J. Med. Chem., vol. 12 (1969) pp. 21–25.
M. J. Gallagher and H. Noerdin, Australian Journal of Chemistry, 38, 997 (1985).
Chemical Abstracts, 104, 648 (148400s) (1986).
Chemical Abstracts, 103, 68(7200p) (1985).
Patent Abstracts of Japan, 12, 163(63-139158(A)) (1988).

*Primary Examiner*—Richard L. Raymond

[57] ABSTRACT

This invention relates to alkylamino and alkyl amino alkyl diarylketones of the formula

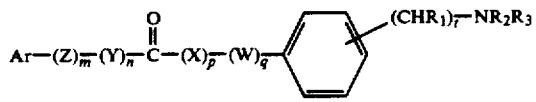

where Ar is aryl of the formula

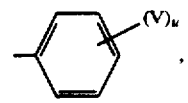

where V is hydrogen, halogen, loweralkyl, loweralkoxy, $CF_3$, $NO_2$ and u is an integer of 1 to 3; X and Y are independently $CH_2$—, —$CH_2$— or —CHF—; Z and W are independently —$CH_2$—, —O—, —CHOH—, or —CHF—; m, n, p, q and t are integers which are independently 0 or 1; $R_1$ is H or loweralkyl; $R_2$ and $R_3$ are loweralkyl; and the pharmaceutically acceptable acid addition salts thereof and where applicable the geometric and optical isomers and racemic mixtures thereof. The compounds of this invention display utility as analgesic agents and as agents for alleviating various memory dysfunctions, characterized by a decreased cholinergic function, such as Alzheimer's disease.

REEXAMINATION CERTIFICATE ISSUED UNDER 35 U.S.C. 307

THE PATENT IS HEREBY AMENDED AS INDICATE BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 4, 5, 12 and 21 are cancelled.

Claims 2, 6–9, 11, 13–15, 17, 19, 22 and 23 are determined to be patentable as amended.

Claims 3, 10, 16, 18 and 20, dependent on an amended claim, are determined to be patentable.

New claim 24 is added and determined to be patentable.

2. The compound [as defined in claim 1] which is 2-(3-chlorophenyl)-1-[3-dimethylamino)methylphenyl]ethanone and the pharmaceutically acceptable acid addition salts thereof.

6. The compound as defined in claim [1] *24* which is 1-(3-chlorophenyl-3-[3-(dimethylamino)phenoxy]-2-propanone and the pharmaceutically acceptable acid addition salts thereof.

7. The compound as defined in claim [1] *24* which is 2,2-difluoro-1-[4-(dimethylamino)phenyl]-2-phenylethanone and the pharmaceutically acceptable acid addition salts thereof.

8. The compound as defined in claim [1] *24* which is 2-(3-chlorophenyl)-2,2-difluoro-1-[4-(dimethylamino)phenyl]ethanone and the pharmaceutically acceptable acid addition salts thereof.

9. The compound as defined in claim [1] *24* which is 2-(3-chlorophenyl)-2,2-difluoro-1-[3-(dimethylamino)phenyl]ethanone and the pharmaceutically acceptable acid addition salts thereof.

11. The compound as defined in claim [1] *24* which is 1,1-difluoro-3-[3-(dimethylamino)phenyl]-1-phenyl-2-propanone and the pharmaceutically acceptable acid addition salts thereof.

13. The compound as defined in claim [1] *24* which is 2-(3-chlorophenoxy)-1-[3-(dimethylamino)phenyl]ethanone and the pharmaceutically acceptable acid addition salts thereof.

14. The compound as defined in claim [1] *24* which is 1-(3-chlorophenyl)-2,2-difluoro-3-hydroxy-3-[3-(dimethylamino)phenyl]propanone and the pharmaceutically acceptable acid addition salts thereof.

15. The compound as defined in claim [1] *24* which is 3-(3-chlorophenyl)-2,2-difluoro-3-hydroxy-1-[3-(dimethylamino)phenyl]propanone and the pharmaceutically acceptable acid addition salts thereof.

17. The compound as defined in claim [1] *24* which is 3-(3-chlorophenyl)-2,2,3-trifluoro-1-[3-(dimethylamino)phenyl]propanone and the pharmaceutically acceptable acid addition salts thereof.

19. The compound as defined in claim [1] *24* which is 3,3-difluoro-4-hydroxy-4-[3-(dimethylamino)phenyl]-1-phenyl-2-butanone and the pharmaceutically acceptable acid addition salts thereof.

22. The compound as defined in claim [1] *24* which is 2-(3-chlorophenyl)-2-fluoro-1-[4-dimethylamino)phenyl]ethanone and the pharmaceutically acceptable acid addition salts thereof.

23. A pharmaceutical composition comprising a compound as defined in claim [1] *24* present in an amount effective for alleviating a memory dysfunction, characterized by decreased cholinergic function, or present in an analgesically effective amount and a suitable carrier therefor.

*24. An alkylamino, alkylaminoalkyl diarylketone of the formula*

*wherein*

*(a) $R_1$ is H or loweralkyl;*

*(b) $R_2$ and $R_3$ are loweralkyl;*

*(c) $Y^1$ is $-CH_2-$, $-CHF-$, $-CF_2-$, $-OCH_2-$, $-CHOHCF_2-$, or $-CHFCF_2$;*

*(d) $W^1$ is $-CH_2-$, $-CH_2O-$, or $-CF_2CHOH-$;*

*(e) V is H, halogen, loweralkyl, loweralkoxy, $CF_3$, or $NO_2$;*

*(f) u is 1, 2, or 3;*

*(g) $n^1$ is 0 or 1;*

*(h) $q^1$ is 0 or 1; and*

*(i) t is 0 or 1, with the proviso that when $q^1$ is 0 and t is 0 or 1, $n^1$ is 1 and $Y^1$ is $-CHF-$, $-CF_2-$, $-OCH_2-$, $-CHOHCF_2-$, or $-CHFCF_2-$; the pharmaceutically acceptable acid addition salts thereof and where applicable the geometric isomers, or optical isomers and racemic mixtures thereof.*

* * * * *